United States Patent
Freydl

(10) Patent No.: US 10,160,572 B2
(45) Date of Patent: Dec. 25, 2018

(54) BAG FOR CARRYING OUT DILUTION SERIES, RECEIVING DEVICE, DISPENSER, METHOD FOR CARRYING OUT DILUTION SERIES, USE OF BAGS FOR CARRYING OUT DILUTION SERIES AND DILUTION SERIES SYSTEM

(71) Applicant: INLABTEC AG, St. Gallen (CH)

(72) Inventor: Ernst Freydl, St. Gallen (CH)

(73) Assignee: iNLABTEC AG, St. Gallen (CH)

( * ) Notice: Subject to any disclaimer, the term of this patent is extended or adjusted under 35 U.S.C. 154(b) by 0 days.

(21) Appl. No.: 14/423,498

(22) PCT Filed: Aug. 26, 2013

(86) PCT No.: PCT/EP2013/067604
§ 371 (c)(1),
(2) Date: Feb. 24, 2015

(87) PCT Pub. No.: WO2014/033079
PCT Pub. Date: Mar. 6, 2014

(65) Prior Publication Data
US 2015/0210435 A1  Jul. 30, 2015

(30) Foreign Application Priority Data
Aug. 29, 2012  (EP) .................................... 12182109

(51) Int. Cl.
*B65D 33/00* (2006.01)
*B65B 3/26* (2006.01)
(Continued)

(52) U.S. Cl.
CPC ................ *B65D 33/00* (2013.01); *B65B 3/17* (2013.01); *B65B 3/26* (2013.01); *G01N 1/38* (2013.01)

(58) Field of Classification Search
CPC .......... B65D 33/00; B65D 75/42; B65B 3/17; B65B 3/26; B65B 9/023; G01N 1/38;
(Continued)

(56) References Cited

U.S. PATENT DOCUMENTS 4,278,198 A * 7/1981 Norton ...................... A61J 1/10
383/119
4,709,534 A  12/1987 Sengewald
(Continued)

FOREIGN PATENT DOCUMENTS

EP  0 096 191 A1  12/1983

OTHER PUBLICATIONS

Balentine C. W. et al., The pre-and post-grinding application of rosemary and its effects on lipid oxidation and color during storage of ground beef:, Meat Science, Elsevier Science, Bd. 73, No. 3, Jul. 1, 2006.
(Continued)

*Primary Examiner* — Christopher Demeree
(74) *Attorney, Agent, or Firm* — Davis & Bujold PLLC; Michael J. Bujold

(57) ABSTRACT

A bag (1) for carrying out dilution series comprises at least one receiving area (2) for the addition of sample and/or dilution liquid, and at least one mixing area (3) for collecting and mixing sample and dilution liquid. The at least one mixing area (3) is closed in a liquid-tight manner on at least three sides, and the receiving area (2) delimits the mixing area (3) on one side.

10 Claims, 12 Drawing Sheets

(51) Int. Cl.
   *B65B 3/17*      (2006.01)
   *G01N 1/38*      (2006.01)
(58) Field of Classification Search
   CPC .............. B29C 66/53262; B01D 29/27; B29L
                              2031/7148; A61D 19/022
   USPC ........................ 383/38, 41; 141/10, 114, 313
   See application file for complete search history.

(56) References Cited

U.S. PATENT DOCUMENTS 5,664,399 A      9/1997  Cassou
   8,506,164 B2 *   8/2013  Lecointe .................. A61J 1/06
                                                          383/22

OTHER PUBLICATIONS http://ww.inlabtec.com/img/pool/2013_09_28_inlabtec_serial_diluter_ba_d.pdf, Sep. 28, 2013, (To Follow).

\* cited by examiner

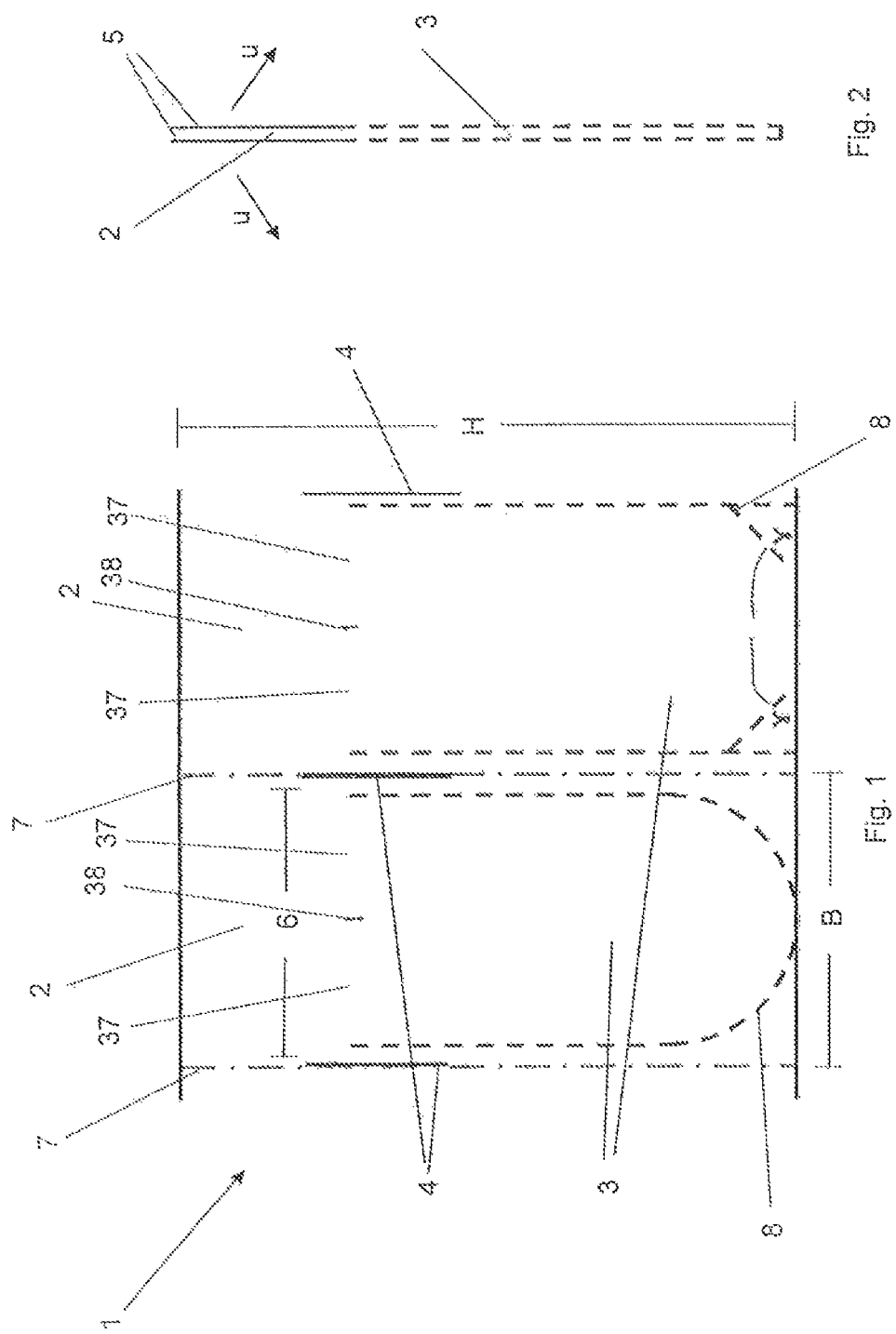

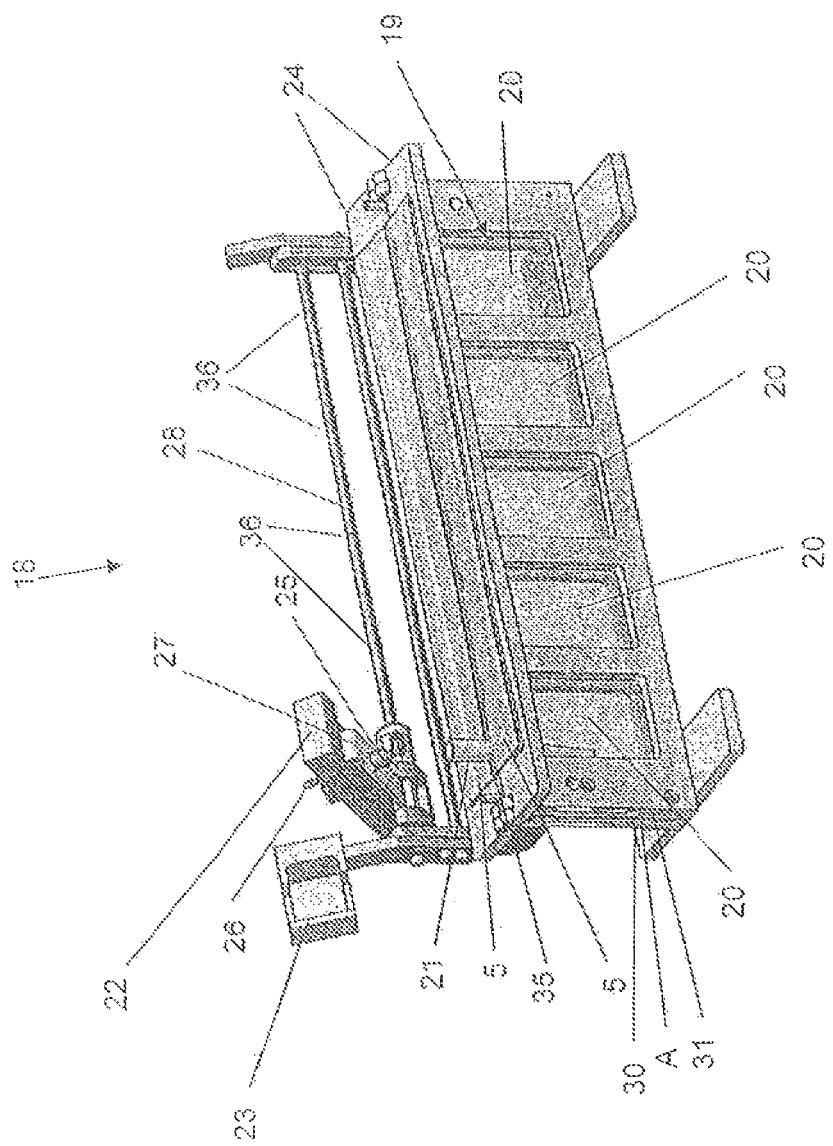

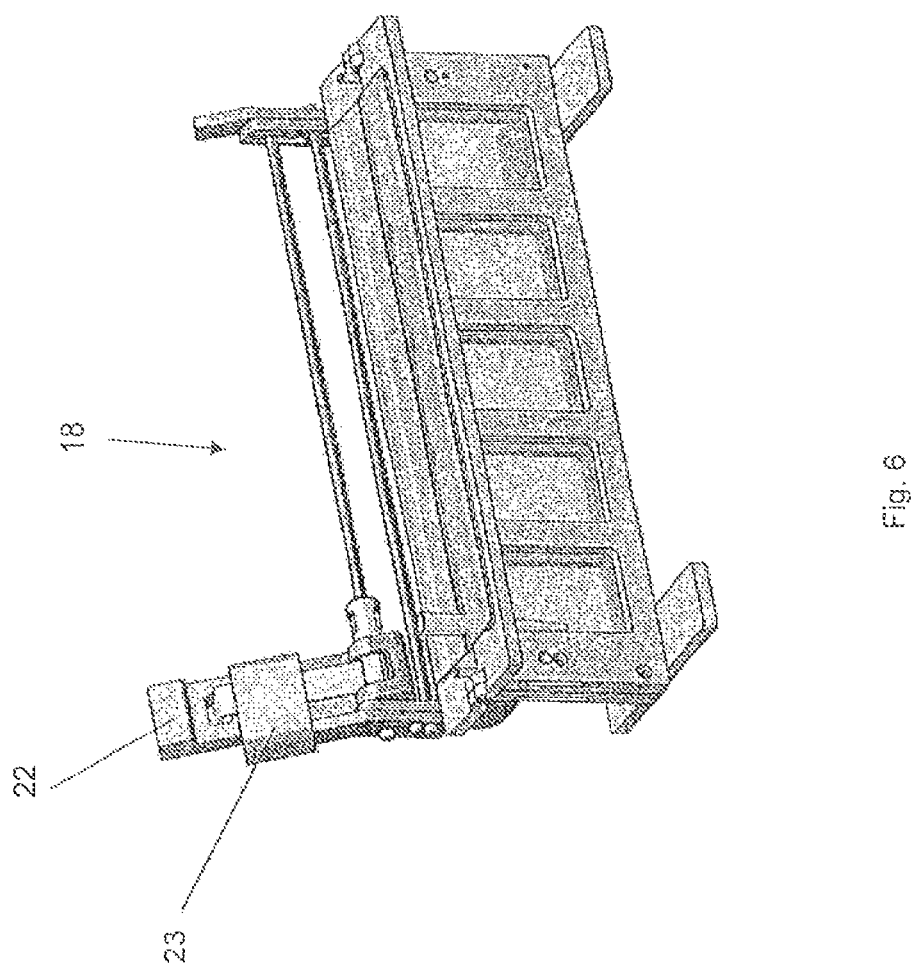

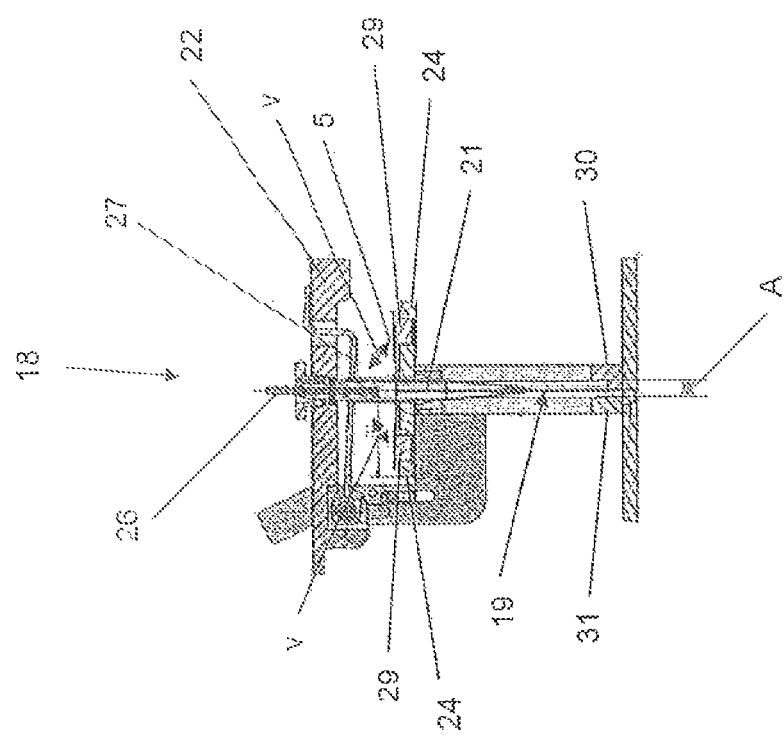

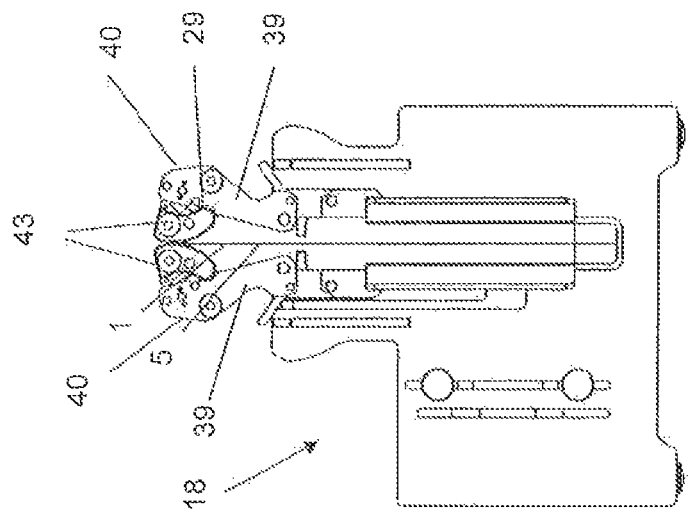
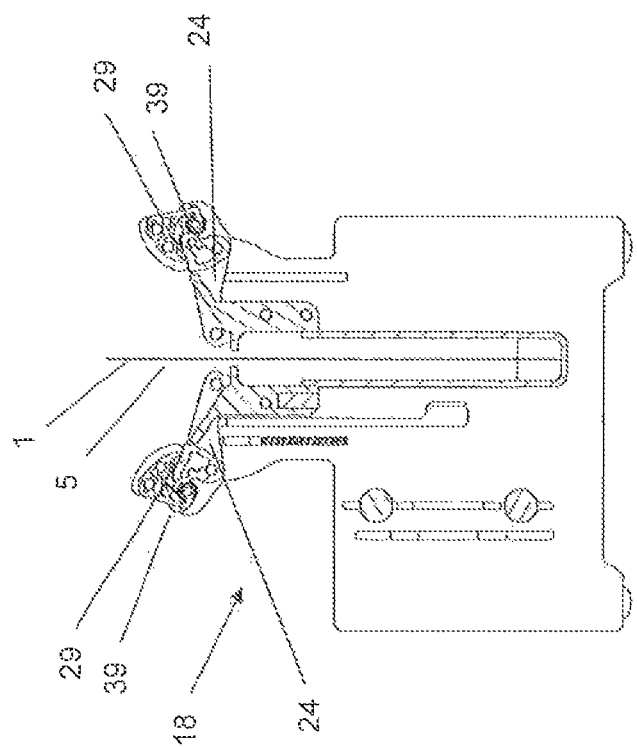

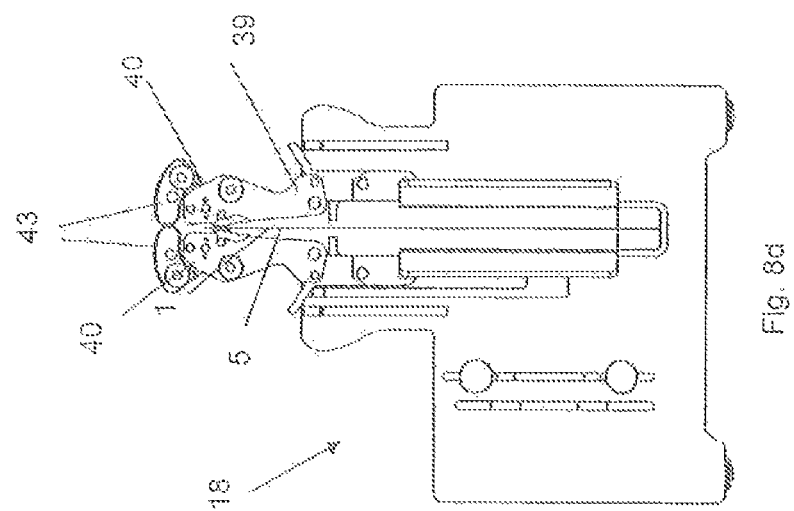
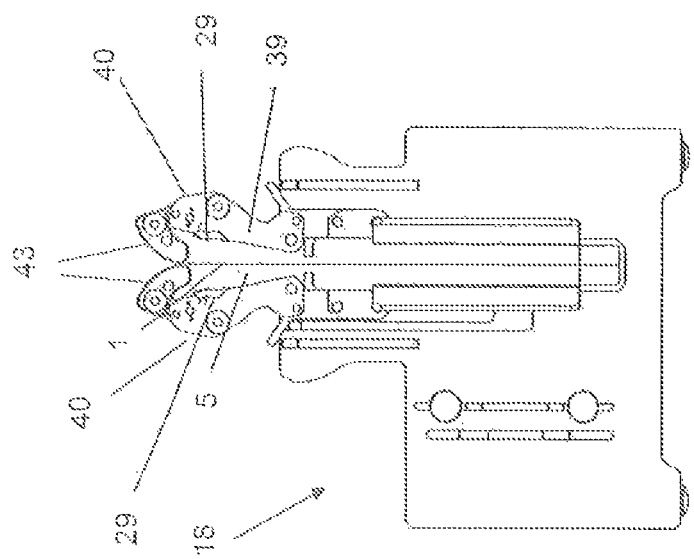

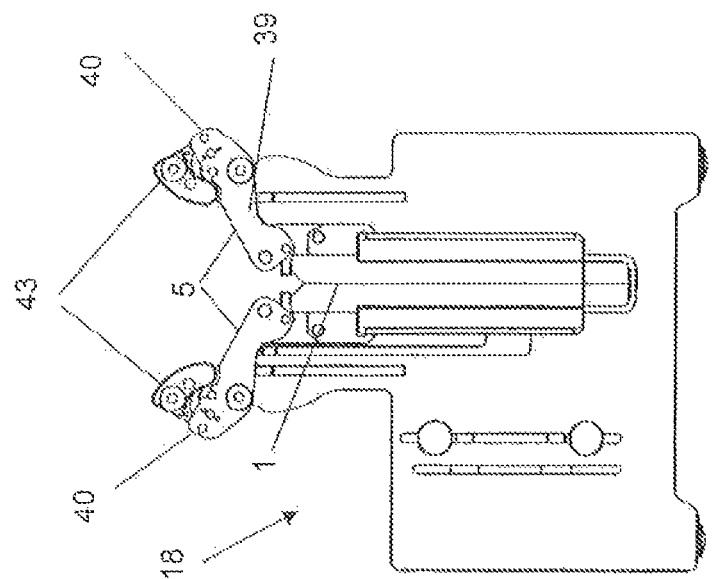
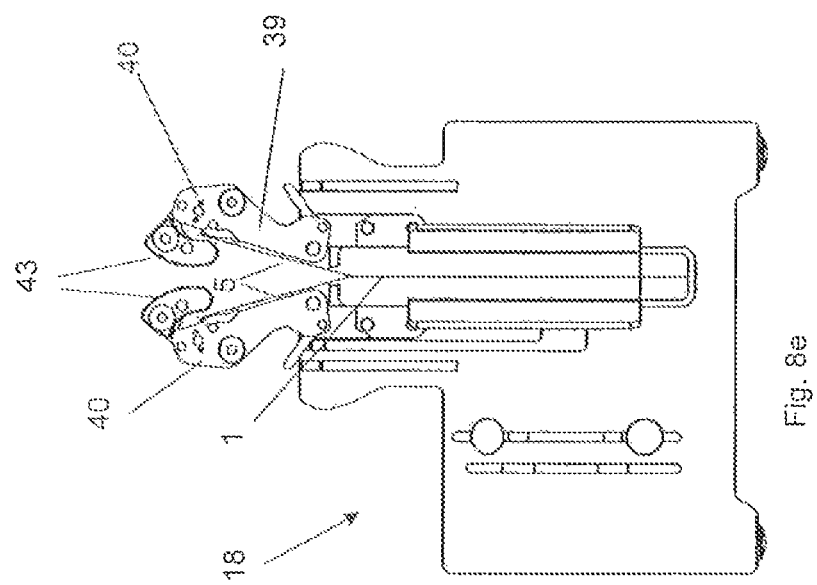

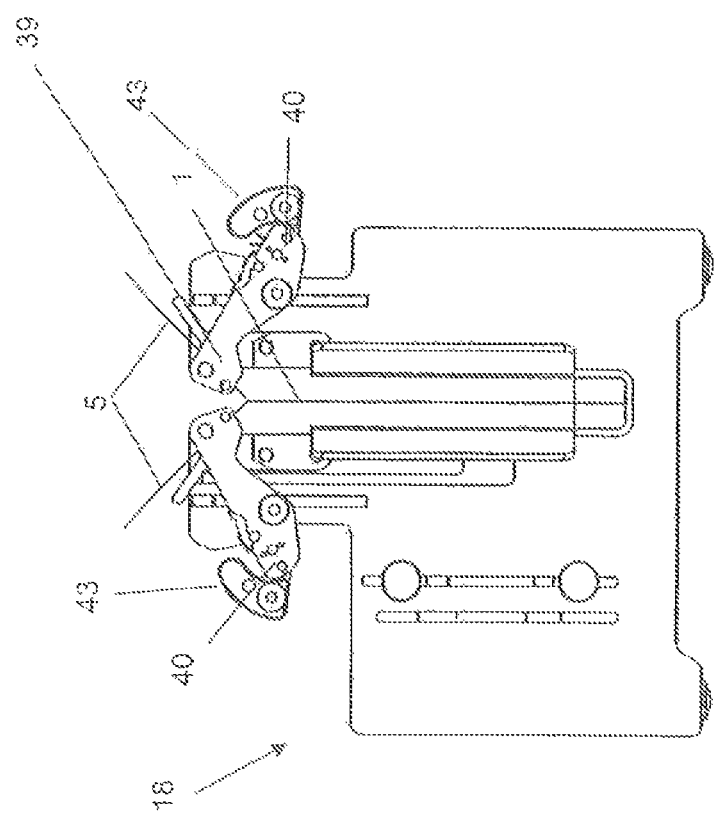

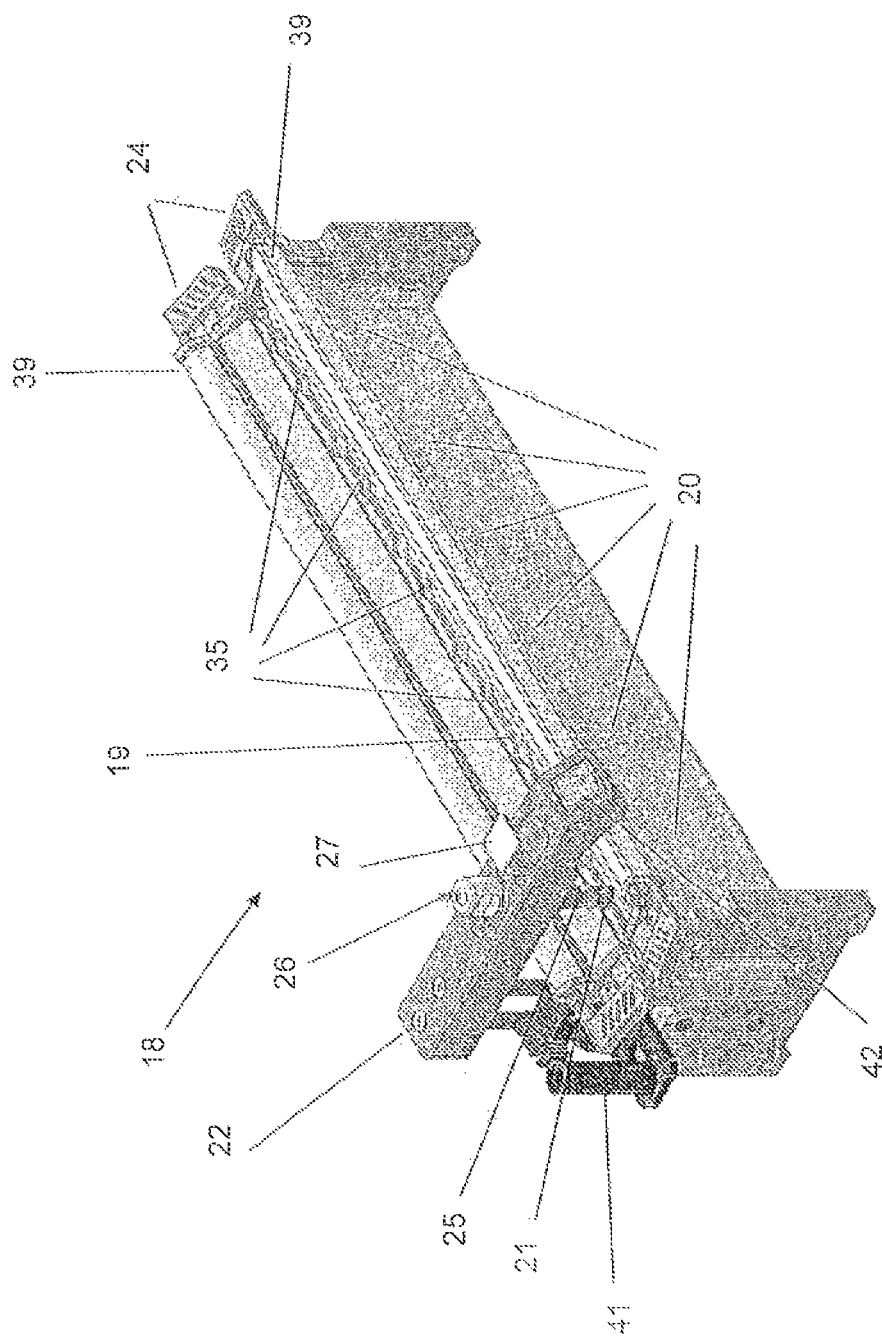

BAG FOR CARRYING OUT DILUTION SERIES, RECEIVING DEVICE, DISPENSER, METHOD FOR CARRYING OUT DILUTION SERIES, USE OF BAGS FOR CARRYING OUT DILUTION SERIES AND DILUTION SERIES SYSTEM

This application is a National Stage completion of PCT/EP2013/067604 filed Aug. 26, 2013, which claims priority from European patent application serial no. 12182109.4 filed Aug. 29, 2012.

FIELD OF THE INVENTION

The invention relates to a bag for carrying out dilution series, to a receiving device for receiving bags for carrying out dilution series, to the use of bags for carrying out dilution series, to a dispenser, to a dilution series system as well as to a method for carrying out dilution series having the features of the preamble of the independent claims.

BACKGROUND OF THE INVENTION

A dilution series is a plurality of solutions which have been produced for a purpose from a concentrated starting solution as a result of dilution. These types of dilution series are produced, for example, in microbiology tor counting bacteria. In order to enable bacteria to be counted, neither too many nor too few bacteria must be cultivated. As a result of producing a dilution series, the original concentration of bacteria can be traced back from the diluted medium.

Diluter systems which absorb the sample into the dilater system and determine the volume of the dilution liquid by means of volume determining on a vacuum pump are known additionally from the prior art (see BioDiluter of July). These types of systems are very labor-intensive and time-consuming to clean and are consequently very expensive.

In order to enable precise determination of the number of bacteria, clean operation is necessary and all the parts which come into contact with the medium containing the bacteria have to be sterile. This results in very costly cleaning processes. In addition, homogeneous mixing of the sample with the diluent is important.

SUMMARY OF THE INVENTION

It is consequently the object of the invention to avoid the disadvantages of the prior art and in particular to create an aid for carrying out dilution series, the use of the aid for carrying out dilution series, a receiving device for receiving aids for carrying out dilution series, a dispenser for dispensing dilution liquid, a system for carrying out dilution series as well as a method for carrying out dilution series which allow rapid and uncomplicated production of dilution series and reduce the time and labor spent on cleaning and consequently reduce the costs involved.

The object is achieved by a bag for carrying out dilution series, the use of a bag for carrying dilution series, a receiving device for receiving bags for carrying out dilution series, a dispenser for dispensing dilution liquid, a system tor carrying out dilution series as well as a method for carrying out dilution series according to the independent claims.

A bag for carrying out dilution series which comprises at least one receiving region for adding sample and/or dilution liquid and for removing diluted medium, is provided to achieve the above-specified object. In addition, the bag comprises at least one mixing region for collecting and mixing sample and dilution liquid, wherein the at least one mixing region is sealed in a liquid-tight manner on three sides and the receiving region delimits the mixing region on one side.

The three sides sealed in a liquid-tight manner correspond according to the invention to the minimum number of sides which have to be sealed in order to hold a liquid in a bag. It would obviously also be conceivable, for example by adding further sides, to provide more sides that are sealed in a liquid-tight manner.

A bag of this type can receive in each case a liquid charge which includes, in a preferred manner, sample and dilution liquid for producing a dilution series, is sterile and does not have to be cleaned. This reduces the time and labor used for cleaning.

The bag can be developed so as to be non-self-supporting. Non-self-supporting within the framework of the application means that the bag is not capable of standing on its own.

This reduces the space required during storage.

The bag can include two foils.

A bag made from two foils is easily producible and requires little space for storage.

The bag can be connected along the three sides, in particular welded.

As a result of a connection on three sides, a bag can easily be produced from foils. Welding, in particular in the case of plastics material foils is a cost-efficient and rapid manner in which to connect the three sides.

The receiving region can comprise at least one, in a preferred manner two tongues which can be folded over.

A tongue simplifies the opening of the bag and enables access to the mixing region.

The at least one tongue can be realized along the entire length of the receiving region.

Consequently, reliable access to the mixing region can be obtained along the entire length of the receiving region. In addition, it would be possible to realize in each case a tongue in the center of the receiving region such that, as a result of the central arrangement, the entire length can also be opened as access to the mixing region. In addition, individual tongues can be realized for each pipette tip port to the mixing region. A pipette tip port within the framework of the invention is an opening in the bag into which a pipette tip can be inserted. In ail cases, the tongues must be realized such that they enable access to the mixing region.

The connection, in a preferred manner a welding, on the sides of the mixing region does not include in a preferred manner the sides of the receiving region. Consequently, the receiving region can be opened and moved freely.

The receiving region can include two pipette tip ports which are realized separately from one another as a result of a connection, in a preferred manner a spot weld. Consequently, the respective pipette tip port can be opened independently of the other one and the pipette tip port not being used in each case remains closed. Consequently, hygienic handling is facilitated.

The bag can include a plurality, in a preferred manner five, in a particular preferred manner six, receiving regions and/or mixing regions. Consequently, the bag can be adapted to the type of dilution series and allows a dilution series to be carried out in a bag.

A first receiving region, in a preferred manner all adjacent receiving regions, can be realized so as to be severable from a second receiving region or from one another. The severability can be developed, in a preferred manner, as a result of a perforation. Consequently, a bag can be prepared simply and rapidly for a certain dilution series by the preferred number of receiving region being able to be severed off.

The receiving region can be developed such that no dead corners are realized and intermixing is promoted by vortex generation. In a preferred manner, the receiving region comprises beveled edges, in particular welding seams, or the receiving region comprises semicircular welding seams which are arranged on the bag opposite the receiving region. Consequently, reliable and complete intermixing of sample and dilution liquid in the bag can be ensured.

The severed connection between each of the receiving regions can be interrupted by an interruption, for example a slit which, in a preferred manner, extends over at least 25% of the height of the bag. An interruption of this type is realized, in a preferred manner, in the region of the pipette tip ports along a line of separation. An interruption of this type enables the mixing region to bulge and consequently facilitates the filling of the mixing region with sample and/or dilution liquid.

A height of the bag is at least 50 mm and a maximum of 150 mm, in a preferred manner at least 70 mm and a maximum of 130 mm, in a particularly preferred manner a maximum of 110 mm and a minimum of 80 mm. A width of the receiving region is a maximum of 70 mm, in a preferred manner a maximum of 52 mm and in a particularly preferred manner a maximum of 45 mm. The volume of the bag can be between 1 ml and 15 ml, in a preferred manner 10 ml.

In the event of the receiving region having beveled edges, the width of the receiving region in each case includes the width in a non-beveled region. A bag of this type of size is optimally suited to carry out a microbiological dilution series.

The receiving regions can be arranged side by side. Side by side within the meaning of the application means side by side in a row. Consequently, a bag comprises at least a first receiving region and a last receiving region, both of which border onto precisely one receiving region. All further receiving regions between the first and the last receiving region border in each case on two adjacent receiving regions. The receiving regions can border onto one another along their entire length or only along a part region. Receiving regions and mixing regions are consequently arranged in each case side by side.

A bag of this type can be produced as an endless strip and inserted into a receiving device provided for this purpose. In addition, a bag of this type can easily be disposed of after use.

In addition, it would be possible to realize a bag with mixing regions which are arranged side by side in a star-shaped manner. In the case of a star-shaped realization, all the receiving regions of a bag comprise a common contact point at a central point. The receiving regions are arranged pointing radially away from said central point.

The bag can consist of polyethylene. In a preferred manner, the bag consists of high-density polyethylene (PE-HD) or a mixture of HD-PE (high-density PE) and LD-PE (low-density PS). In addition, PP (polypropylene), PVC (polyvinyl chloride), PS (polystyrene) and transparent foils or bio-based plastics material foils made of polyactide (PLA) or thermoplastic starch (TPS) would also be possible, for example, as material. A bag of this type can be produced in a cost-efficient and easy manner and can be easily disposed of.

In addition, there are no reactions with the sample or the diluent. The bag can consist of a transparent material.

Consequently, the filling and mixing inside the bag can also be visibly controlled. The wall thickness of the bag is within the range of between 15μ and 30 μm.

Consequently, an optimum ratio between material consumption and the strength of the bag is obtained.

A material of the bag can comprise a density of between 0.8 and 1.2 g/cm$^3$, in a preferred manner 0.9 g/cm$^3$. A bag of this type is easy to store and can be easily inserted into a receiving device.

The bag can be realized so as to be able to be rolled up and/or folded up and placed into packaging. Consequently, the bag is easy to stow, easy to sterilize and can foe transported in a sterile manner to its target destination.

The bag can be realized in a sterile manner. Consequently, correct dilution series can be obtained.

The bag as described previously can be used for carrying out dilution series or in further laboratory applications.

A receiving device for receiving bags for carrying out dilution series, in particular for receiving bags as described previously, is provided to achieve the previously named object. The receiving device includes a loading region for a bag with at least one receiving region, wherein the loading region comprises a receiving portion for each receiving region of a bag. In addition, at least one holding device is realized for a side or tongue of a bag.

A receiving device of this type enables a bag to be received in a sturdy manner and consequently a dilation series to be carried out in a reliable and simple manner. This is in particular as a bag itself is not capable of standing and consequently cannot be filled unaided in a reliable manner without support or fastening. The receiving device is realized in a preferred manner such that a bag in a loaded state touches the bottom of the receiving device such that the weight of the bag with contents does not have to be held exclusively by the holding device. Furthermore, it is possible in addition to this or as an alternative to it, to clamp the bag in the receiving device such that the bag is fixed in the receiving device.

The holding device can be realised so as to be movable such that the position of a contact surface between the holding device and the bag is realized so as to be adjustable in neighs with reference to the loading region and in a preferred manner in a spacing between the contact surfaces. Consequently, stress occurring onto the tongues of the bag as a result of reducing the spacing between the contact surfaces can be reduced and the durability and reliability of the bag is increased.

A holding device of this type facilitates the holding of a bag inside the receiving device and secures the bag during filling. The ability to move the contact surfaces of the holding device between the holding device and the bag reduces the formation of stresses on the bag and thus enables more reliable operation.

The holding device can include an adhesive, in a preferred manner on the contact surfaces, which mates adhesion with a bag, in a preferred manner with a tongue of a bag, achievable.

With a holding device of this type, a bag can be opened and held in an easy and reliable manner without incurring the risk of, for example, destroying the bag as a result of clamping.

The adhesive, in a preferred manner, includes a permanently adherent or glueable material which can be washed, in a particularly preferred manner a low cross-linked PUR (polyurethane) such as, for example, a PUR gel or a PUR casting resin. A material which, on account of its surface characteristics, achieves adhesion in a mechanical manner or by means of van der Waals forces, is used in a preferred manner. This can be, for example, silicone with microscopic elements on the surface which allow adhesion by means of van der Waals forces. For example, Gecko-Nanoplast produced, by Gottlieb Binder GmbH, D-71084 Holzgerlingen can be used.

As an alternative to this or in addition to it, the holding device can include a flap mechanism by way of which a mechanical gripping force is achievable on the tongues of a bag. Consequently, the fastening of the bag in the receiving device is optimized.

The flap mechanism includes flaps which comprise a contact surface by way of which adhesion to a bag can be achieved. The flaps can be moved toward one another from a starting position such that tongues of a bag are moved into contact with the contact surface. When the flaps are opened back into the start position, the bag is opened and the interior of the bag made accessible.

To release the bag, the flaps can be pressed in a preferred manner against a spring force away from the bag tongues. The tongues of the bag thus remain suspended on a fixed pipette table and are released from the contact surface. The spring force then presses the flaps into the start position again.

The flap mechanism can additionally include side parts which, in addition to the adhesive force of the contact surfaces, make a gripping force on the tongues of the bag achievable.

The side parts can be mounted so as to be resilient about a pivot axis such that when the flaps move out of the starting position toward one another, said side parts are moved away from the contact surface against the spring force. In this connection, the pivot axis does not correspond to the center point of the radius of the curved side surface of the side parts. The pivot axis is consequently arranged in an eccentric manner with respect to the pivot point of the radius of the side parts. As a result, a tongue of a bag can come into contact with the contact surface. In the case of the subsequent opening of the flaps back into the starting position, the side part are moved back into their first position as a result of the spring force of the spring and grip the tongues of a bag.

In a preferred manner, the flap mechanism is realized such that in addition the removing of the bag out of the receiving device is made easier by the holding device being able to assume an output position in which the adhesion of the contact surfaces with the tongue of the bag and the mechanical gripping force are released.

The receiving device can include a dosing head for adding dilution liquid, wherein the dosing head is connectable to a liquid source and is realized so as to be able to be inserted into an opening, in particular a pipette tip, for dispensing the liquid. The dosing head in a preferred manner comprises contamination guard and is realized in a particularly preferred manner so as to be displaceable along an axis of the receiving device. As a result of the displaceability, each loading region can be operated by the dosing head.

In a preferred manner, the opening for dispensing liquid is a pipette tip such that the dosing head is able to come into contact exclusively with dilution liquid and not with sample. Consequently, a development of this type facilitates the cleaning operation and carryover can be prevented.

A dosing head of this type enables dilution liquid to be added in a very precise and dimensionally accurate manner such that a correct dilution series is able to be produced.

A contamination guard prevents the contamination of the dosing head by the outside air or by other external influences and the displaceability facilitates the adding of dilution liquid in a very precise manner.

The loading region can comprise at least one insertion point for a pipette tip, in a preferred manner an adjustable insertion point. In a preferred manner at least one adjustable insertion point is realized per receiving portion.

An insertion device enables the insertion of a pipette tip, as well as at the same time enabling the pipette tip to be fixed such that a dosing head is able to be placed onto the pipette tip. An adjustable insertion point is adaptable to different sizes of pipette tip. As a result of at least one adjustable insertion device per receiving portion, each receiving portion can be reached with a pipette tip and the dosing head can be coupled to the pipette tip in each receiving portion.

An insertion point of this type facilitates the handling and consequently enables correct clean operation.

The loading region can Include a removal opening which is realized such that a pipette tip wish a predefined length extends down as far as the lowest point of the loading region.

A removal opening of this type enables the removal of dilution liquid with sample without the risk of carrying over sample material which has been added through the insertion point.

The receiving device, in a preferred manner the dosing head can additionally include a triggering element which, when actuated, triggers the pipette operation. A triggering element of this type can be realized mechanically or electrically. In a preferred manner, there is an electric connection to a dispenser for the triggering process.

A triggering element on the receiving device facilitates handling during the pipetting operation.

A dispenser for dispensing dilution liquid, said dispenser including a receiving means for a pipette for receiving and measuring the dilution liquid, is provided in addition to achieve the above-specified object. In addition, the dispenser includes a receiving means for a feed line from the dilution liquid to the pipette, a receiving means for removing dilution liquid from a pipette and a vacuum source for generating negative pressure in the pipette for aspirating the dilution liquid.

A dispenser of this type enables the precise addition of dilution liquid and is easy to clean because all the parts, such as tubes and pipette are easily exchangeable and do not come into contact with contaminated liquid.

The dispenser can comprise a fill level sensor, by means of which the liquid volume can be determined on the pipette.

Consequently, the addition of the liquid volume can be measured directly on the pipette such that precise determining is possible as well as a visual check.

The pipette can be exchangeable. The pipette can be loaded into the receiving means for a pipette and as a result of a clip-connecting or snap-connecting mechanism can easily be removed and re-inserted.

Consequently, a commercially available pipette such as, for example, a serological pipette made of plastics material or glass can be clamped in the dispenser such that replacement parts can be easily available and the volume of the pipette can be easily adapted to the requirements.

A pressure source can be realized for generating a pressure for dispensing the dilution liquid out of the pipette, wherein the pressure source in a preferred manner is a pressure pump in combination with a pressure tank.

In this connection, the pressure tank supports the dispensing of the dilution liquid at the start of the dispensing process in order to enable the dilution liquid to be dispensed in a rapid manner. The pressure tank can be loaded with compressed air in a preferred manner during the drawing of the dilution liquid into the pip-elite and the pressure can be unloaded from the pressure tank to support the dispensing process during the dispensing of the dilution liquid. The last volume parts of the dilution liquid are dispensed substantially exclusively by means of pressure from the pressure source, in a preferred manner by means of pressure from the pressure tank, slightly supported by the pressure pump such that the dilution liquid does not spray out of the pipette at excessive pressure.

This type of realization enables rapid dispensing of the dilution liquid which nevertheless occurs in a controlled manner.

The fill level sensor can be an optical fill level sensor.

An optical fill Level sensor is accurate and nevertheless cost-efficient.

As an alternative to this, a capacitive or ultrasound sensor would also be conceivable.

The dispenser can comprise sterile filters, in particular at a contact point between a tank of dilution liquid and the outside air and at a contact point between the pipette and contaminated air in order to prevent contamination of the dilution liquid by contaminated air.

A sterile filter is consequently mounted in a preferred manner at all contact points between the dilution liquid and the air.

A dispenser which is developed in this manner enables clean, germ-tree and correct operation.

The pipette can comprise a scale on which the accuracy of the fill level sensor can be checked.

A scale of this type enables simple visual checking on the accuracy and also enables the fill level to be adapted to the desired level if necessary.

Tubes can be placed into the dispenser. The tubes, in a preferred manner, are arranged between a tank of dilution liquid and the pipette and between the pipette and the dilution series arrangement or dosing head of a receiving device. The tubes can be placed in pinch valves which, on the one hand, form the support for the tubes and, on the other hand, have a valve function.

The tubes conduct dilution liquid into the pipette and out of the pipette to a dilution series. The use of tubes makes said connections easily exchangeable and easily cleanable.

The dispenser can include pinch valves by way of which the feeding and dispensing of dilution liquid can be controlled.

The pinch valves enable or prevent liquid running through a line.

The pinch valves are simple to handle, favorable to purchase and easy to maintain. In addition, pinch valves make it simple to dismantle and exchange the lines, in particular tubes.

The dispenser can include a height-adjusting means tor the pipette receiving means which mates adapting a pipette holder to the height of the pipette inserted achievable.

Height-adjusting means for the dispenser enables different sizes of pipettes to be inserted and consequently the dispenser to be adapted to different volumes.

The dispenser can be operable in a load mode in which tubes and pipette can be removed and inserted. In a load mode of this type, all the valves are open such that the tubes can be removed. In addition, in a preferred manner there is no vacuum in a load mode. A mode of this type enables rapid cleaning of the dispenser and rapid exchanging of damaged parts if necessary.

In addition, the dispenser can be operable in a correction mode in which the fill level of dilution liquid in the pipette can be adjusted.

In said correction mode, the valve which adjusts the feeding of dilution liquid is opened such that dilution liquid is able to flow out of the pipette back into the liquid tank. As a result, the fill level sensor can be adapted such that the next time the pipette is filled with dilution liquid, the correct volume level can be achieved.

The dispenser can be connectable to a receiving device in an electronic manner.

As a result of an electronic connection between the dispenser and the receiving device, the dispenser can be actuated by triggering elements on a receiving device. The handling is consequently simpler.

The dispenser can additionally include a pressure sensor by way of which a pressure drop can be detected during the dispensing of the dilution liquid.

Consequently, it is ensured that all the dilution liquid has been dispensed and additionally, in a preferred manner, air can be dispensed for the mixing of sample and dilution liquid.

A method for carrying out dilution series is also provided for achieving the above-specified object and includes the following steps:

Draw a predetermined amount of dilution liquid from a tank into a pipette as a result of generating negative pressure in the pipette by means of a vacuum pump;

terminate the drawing in process, in particular by a signal from a fill level sensor on the pipette;

close a valve between the tank and the pipette;

pour, and in a preferred manner simultaneously mix with sample material, the predetermined amount of dilution liquid drawn in from the pipette into a bag for producing dilution series.

A method of this type enables dilution liquid to be added rapidly and precisely to a sample. In addition, no contact takes place between the sample and the pipette or tubes such that in the normal case it is not necessary to clean the dispenser.

The pouring of the dilution liquid into the bag can be supported by a pressure source.

When supported by a pressure source, the dilution liquid is able to be inserted more rapidly into the bag. During the drawing in of the dilution liquid, a pressure tank can be topped up and when filling the dilution liquid into the bag can be used in addition to the pressure of a pressure pump to increase the flow speed of the dilution liquid.

As a result of topping up the pressure tank in dependence on the volume drawn in, in a preferred manner with the air from the pipette during the drawing-in process, no more pressure can be present in the pressure tank than is necessary for dispensing the dilution liquid. Consequently no more pressure can be output either. The pressure tank consequently contributes to the increase in the flow speed of the dilution liquid when filling the dilution liquid into a bag, the absolute pressure for the filling process is reduced, however, toward the end of the volume to be filled such that the air bubbles, which are still added for mixing purposes after the liquid amount is filled into the bag, are not input at the highest pressure.

The use of a pressure tank of this type enables the pressure increase to be adapted simply to the volume used without the dispenser having to be converted or reprogrammed. In addition, the pressure tank enables the dilution liquid to be poured in rapidly without the risk of the dilution liquid and/or sample spraying out of the bag.

After pouring in tine dilution liquid, air can be pressed into the bag through the pipette.

The pressing in of air leads to better mixing of the dilution liquid and sample as a result of the sudden reversal of direction of rotation of the vortex generated.

The pouring of the dilution liquid into a bag can be carried out by means of a dispenser head of a receiving device through a pipette tip.

The use of a dispenser head of a receiving device and a pipette tip enables correct dosing with no contact between the dispenser or the dispenser head and the sample. In addition, the sample is rinsed completely out of the pipette tip. The pipette tip can be disposed of together with the bags after contact with a sample medium, in a preferred manner once the dilution series has been competed.

The above-mentioned object is additionally achieved by a system comprising at least one of the following elements:
  a bag as previously described;
  a receiving device as previously described;
  a dispenser as previously described.

BRIEF DESCRIPTION OF THE DRAWINGS

The invention is explained in more detail below in exemplary embodiments by way of figures, in which:
FIG. 1 shows a schematic view of a bag;
FIG. 2 shows a side view of a schematic view of a bag;
FIG. 5 shows a perspective view of a receiving device;
FIG. 6 shows a perspective view of the receiving device from FIG. 5 in a loading position;
FIG. 7 shows a section through a receiving device;
FIG. 8a shows a section through a receiving device in a starting position;
FIG. 8b shows a section through a receiving device in a first flap position;
FIG. 8c shows a section through a receiving device in a second flap position;
FIG. 8d shows a section through a receiving device in an adhesion position;
FIG. 8e shows a section through a receiving device in a gripping position;
FIG. 8f shows a section through a receiving device in a filling position;
FIG. 8g shows a section through a receiving device in a dispensing position;
FIG. 9 shows a perspective view of an alternative embodiment of the receiving device.

DETAILED DESCRIPTION OF THE PREFERRED EMBODIMENTS

Figure 3:
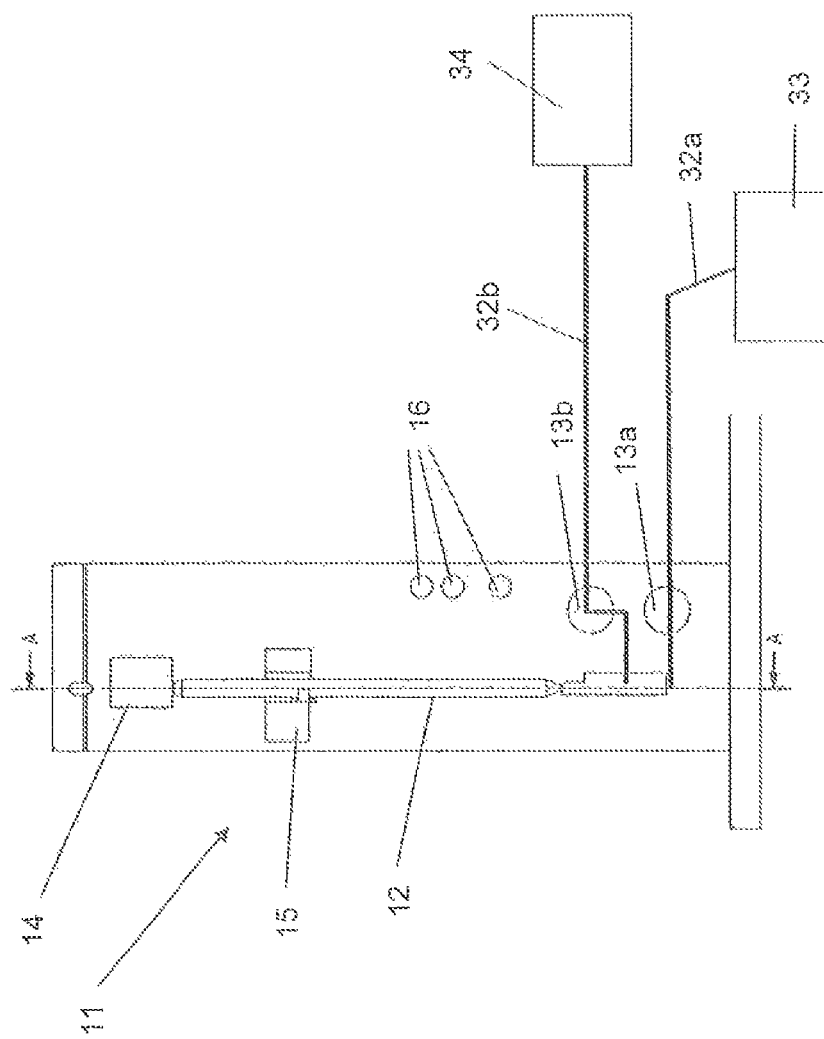
FIG. 3 shows a schematic representation of a dispenser.

FIG. 1 shows a schematic view of a bag 1. The bag 1 shown here comprises as an example two portions lying side by side. The bag 1 includes two receiving regions 2 as well as two mixing regions 3, i.e. one such region each per portion. On each of the three sides, the respective mixing region 3 is sealed in a liquid-tight manner by welding seams and/or folds. The respective mixing regions 3 are realised so as to be able to be severed from one another by means of perforations 7. The connection with the perforation 7 is interrupted by a slit 4. A slit 4 of this type enables the bag to bulge in a facilitating manner when sample and/or dilution liquid is poured in. A punctiform connection in the form of a spot weld 38, by means of which the access into the mixing region 3 is divided into two pipette tip ports 37, is arranged within the region of the transition from the receiving region 2 into the mixing region 3. This enables access to the mixing region 3 with a pipette rip only in a limited region and separate from the next pipette tip. Consequently, carry-over and contamination are prevented. A portion of the bag 1 comprises a width B of 60 mm. The width B is measured from perforation 7 to the next perforation 7. The height H of the bag 1 which includes the mixing region 3 and the receiving region 2, is 110 mm. The proportion of the receiving region 2 at said height is 30 mm, whilst the proportion of the mixing region with the height H is 80 mm. The width 6 of the receiving region 2 extends from one weld to the next weld. The receiving region 2 at the same time forms two tongues (see FIG. 2) which are realized so as to be foldable in arrow direction u. The tongues 5 consequently extend over the entire length of the receiving region 2. There is no longer any liquid-tight connection in the receiving region 2. The bag 1 is realized from foils. The foils are transparent to visible light and are made from polyethylene (PE). The respective mixing regions 3 additionally comprise welding seams which are formed so as to avoid dead corners and to enable vortices to be generated in a targeted manner by means of liquid and air. The first mixing region 3, in this connection, is provided with a semicircular welding seam in the manner of an example. The second mixing region 3 is developed as an example with beveled edges 8. As a rule, the mixing regions are developed identically in an endless bag. The bag 1 is produced as an endless bag and can be severed by the user at the perforations 7 depending on the number of mixing regions 3 required.

The bag 1 is stored in cardboard packaging and can also be removed individually through a removal opening. In addition, the bag 1 is gamma sterilized and also packaged in a sterile manner in the cardboard packaging.

FIG. 2 shows a side view of the bag 1 from FIG. 1. The bag 1 comprises a receiving region 2 as well as a mixing region 3. The receiving region 2 is formed by two tongues 5. The tongues 5 are developed so as to be foldable over in arrow direction u.

FIG. 3 shows a schematic view of a dispenser 11. The dispenser 11 includes a pipette 12 which is connected by means of tubes 32a, b which can be controlled by pinch valves 13a, b. A scale is realised on the pipette 12. In addition, the dispenser 11 includes a fill level sensor 15 on the pipette 12. The fill level sensor 15 enables the volume of the liquid in the pipette 12 to be determined. In addition, the dispenser 11 includes a height-adjusting means 14 by way of which the dispenser 11 is able to be adapted to different pipettes 12. The fill level sensor 15 is an optical fill level sensor. The pinch valves 13 enable the interruption or opening of a flow of liquid, on the one hand, from a liquid tank 33 to the pipette 12 and, on the other hand, from the pipette 12 to a dosing head or directly to a pipette tip 34. Both the liquid tank 33 and the pipette are provided with sterile filters which keep incoming air sterile. The pipette 12 can be connected to a vacuum pump above the height-adjusting means 14. The vacuum pump generates a negative pressure and, with the pinch valve 13a open, enables a liquid to be drawing in out of the liquid tank. In addition, the dispenser 11 includes optical indicators which indicate the mode of operation and/or faults.

To produce a dilution series, first of ail dilution liquid is drawn out of a liquid tank 33 by means of a vacuum source into a pipette 12 up to a predetermined fill level. The sufficient filling of the pipette 12 is registered by the fill level sensor 15 and the pinch valve 32a is closed such that no further liquid is drawn into the pipette 12. During the filling of the pipette 12, a pressure tank is topped up by a compressor in dependence on the air escaping out of the pipette 12. To dispense the liquid, the pinch valve 32*b* is then opened and by means of the pressure tank and a pressure source the liquid iron the pipette 12 is added into a bag 1 (see FIG. 1) for creating the dilution series.

Figure 4:
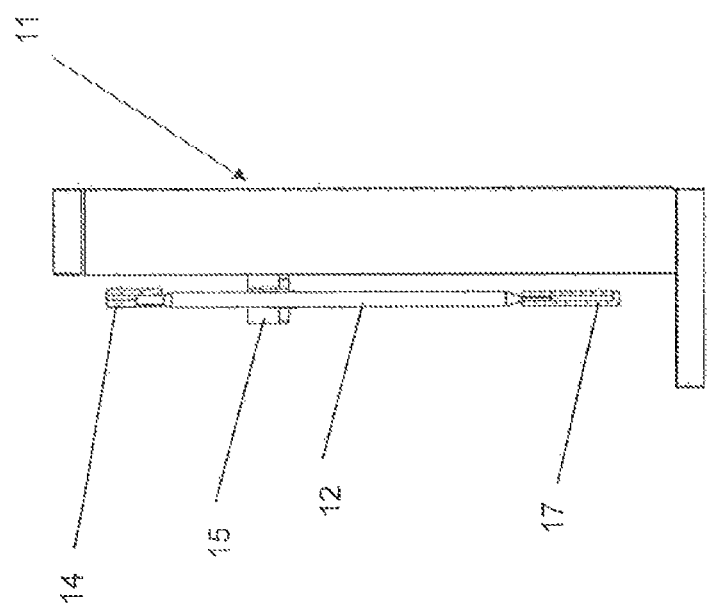
FIG. 4 shows a schematic side view of the dispenser from FIG. 3.

FIG. 4 shows a side representation of FIG. 2. The dispenser 11 includes a pipette 12 on which a scale is recorded. A fill level sensor 15 is mounted on the pipette 12. The top end of the pipette 12 is provided with a height-adjusting means 14 such that different pipettes are able to be inserted into the dispenser 11. A connector 17, which, for example, can include a T-shaped tube piece on which tubes can be mounted, is mounted at the bottom end of the pipette 12.

FIG. 5 shows a perspective view of a receiving device 18. The receiving device 18 includes a loading region 19 into which a bag 1 (see FIG. 1) is loaded. The loading region 19 includes five receiving portions 20. The receiving portions 20 are developed such that the bag 1 (see FIG. 1) is visible in the receiving device 18. In order to enable the visibility, the loading regions include in each case a frame and/or a transparent glass pane, in the recess of which the inserted bag can be seen. The receiving device 18 additionally includes holding devices 24 for the tongues 5 of a bag 1 (see FIG. 1). The holding devices can be hinged and provided with an adhesive such that the tongues 5 adhere to the holding device 24. The pipette tip 21 consequently enables the addition of dilution liquid or sample into a mixing region 3 of a bag 1 (see FIG. 1). The loading region 19 includes a first side wall of the loading region 30 as well as a second side wall of the loading region 31, between which is realized a spacing A. The spacing A is realized so as to be adjustable. Each receiving portion 20 additionally includes a pipette tip receiving means 32 which is realized such that the pipette tip 21 is able to be inserted into the receiving portion up to a stop or a positive locking or non-positive locking receiving means. Consequently, the pipette tip 21 can be deposited in the receiving device without it falling into a bag. The receiving device 18 comprises a dosing head 22 which is realized so as to be displaceable along a rail. In addition, a dosing head 22 can be connected to the pipette tip 21. For this reason, the dosing head 22 comprises a pipette tip connector 25 as well as a feed connector 26 for the feeding of dilution liquid. A release mechanism is actuated in order to release a pipette tip 21 from the dosing head 22. The release mechanism 27 is part of the dosing head 22. The release mechanism 27 is rotationally mounted on one side and can be removed from the dosing head 22 by actuating a pipette tip 21. A pipette tip 21 with a higher grade dilution as well as a second pipette tip 21 with the lower dilution is used for each receiving portion 20. When not in use, the dosing head 22 can be covered by a contamination guard 23 which is connected to the dosing head such that no contamination whatsoever is able to pass onto the pipette tip connector 25. In addition, the dosing head 22 is developed so as to be displaceable by means of the longitudinal displacement rail 28. For this purpose, the longitudinal displacement rail 28 comprises latching positions which position the dosing head 22 in a correct position for the respective receiving portion 20.

FIG. 6 shows the receiving device 18 from FIG. 5, in which the dosing head 22 is covered by the contamination guard device 23.

FIG. 7 shows a section through a receiving device 18. The receiving device 18 comprises a first side of the loading region 30 and a second side of the loading region 31. The sides 30, 31 of the loading region 19 are realized so as to be adjustable such the spacing A can be reduced or enlarged such that different pipette tips 21 can be inserted. The receiving device additionally includes two holding devices 24, the holding devices 24 in each case comprising a contact surface 29. The contact surface 29 includes polyurethane such that a tongue 5 of a bag 1 (see FIG. 1) can be fastened to the contact surface 29 as a result of adhesion. The contact surface 29 is pivotable in a direction v. In addition, the holding devices 24 are resiliently mounted in a preferred manner so as to be adjustable with a spacing between one another such that any tension possibly occurring on a bag which is adhered thereon is able to be reduced. A bag 1 (see FIG. 1) opened in this manner is easily accessible with a pipette tip 21. In said representation, the dosing head 22 is connected to the pipette tip 21. The release mechanism 27 can be actuated in order to release said connection. The dosing head 22 can additionally be connected to a feed connector 26 on a dispenser.

FIGS. 8*a* to 8*g* show the sequence of loading a bag 1 into the receiving device 18. The holding device 24 of the receiving device 18 includes a contact surface 29 which is coated with microstructured silicone. Adhesion can be achieved between the contact surface 29 and the bag 1 as a result of the microstructured silicone. In addition, the holding device 24 includes a flap mechanism 39. The flap mechanism 39 is developed so as to be movable in such a manner that a bag 1 is gripped in a filling position (FIG. 8*f*) by the flap mechanism 39 and is additionally held for adhesion. The sequence of the loading, fixing and dispensing of the bag 1 is given below. FIG. 8*a* shows the receiving device 18 in a starting position. The bag 1 is loaded into the receiving device 18. The tongues 5 of the bag 1 are not in contact with the contact surface 29. In order to hold the bag 1 in the receiving device 18 and to open the tongues 5, the flap mechanism 39 is moved into a first flap position (FIG. 8*b*). In the first flap position, there is a gap between the side parts 43 of the flap mechanism 39 which are offset by the flaps 40. The tongues 5 of the bag 1 are arranged between the two side parts 43, which are arranged between the two flaps 40 of the flap mechanism 39. As a result of pushing the flaps 40 further together against the spring force of the flaps 40 and against the spring force of the side parts 43 of the flap mechanism 39, the side parts 43 of the flap mechanism 39 are moved into the second flap position (FIG. 8*c*) without at the same time the bag 1 being pulled by the tongues 5 out of the device 18 as the gap formed by the side parts 43 is maintained between the two flaps 40 of the flap mechanism 39. The flaps 40 are moved in this connection along a circular path with a center in the flap mechanism 39. An adhesion position is reached (FIG. 8*s*) as a result of pressing the flap mechanism 39 in a more extensive manner. In the adhesion position the flaps 40 of the flap mechanism 39 are completely closed upward, the side parts 43 are completely open and the contact surfaces 29 are in contact with the tongues 5. As a result of the coating of the contact surface 29 with microstructured silicone, adhesion is obtained between the contact surface 29 and the tongue 5 of the bag 1. Once the adhesion between the contact surfaces 29 and the tongues 5 has been obtained, the tongues 5 are pulled apart as a result of the spring force of the flaps 40 being released and at the same time the side parts 43 are moved again in the direction of the starting position. As a result, the side parts 43 grip the tongues 5 on each side and obtain an additional holding force onto the bag 1 in the gripping position (FIG. 8*e*). In the filling position (FIG. 8*f*) the tongues 5 of the bag 1 are then opened so far that a pipette can be inserted into the bag. The tongues 5 are fastened in said position as a result of the gripping of the side parts 43 and adhesion of the contact surface 29. To remove the bag 1 out of the receiving device 18, the flaps 40 are moved into an output position (FIG. 8g) in which the adhesion of the contact surface 29 with the tongues 5 of the bag 1 as well as the gripping force of the side parts is mechanically released. The bag 1 can consequently be easily removed. To release the adhesion, the contact surface 29 is pivoted down from the pipette table 44 as a result of rotating the flaps 40 and is thus detached from the tongue 5.

FIG. 9 shows a perspective view of an alternative embodiment of the receiving device 18. The receiving device 18 includes a loading region 19 into which a bag 1 (see FIG. 1) can be loaded. The loading region 19 includes six receiving portions 20. The receiving portions 20 are developed such that the bag 1 (see FIG. 1) is visible in the receiving device 18. In order to enable the visibility, the loading regions in each cause include a transparent Plexiglas pane, through which the inserted bag can be seen. The receiving device 18 additionally includes holding devices 24 for the tongues 5 (see FIG. 1) of a bag 1 (see FIG. 1). The holding devices 24 are hingeable and provided with microstructured silicone such that the tongues 5 (see FIG. 1) can be adhered to the holding device 24. In addition, the holding device 24 includes a flap mechanism 39 which fixes an inserted bag in addition to the adhesion. The function of the flap mechanism is shown in FIGS. 8a-g. The pipette tip 21 consequently enables the addition of dilution liquid or sample into a mixing region 3 of a bag 1 (see FIG. 1). Each receiving portion 20 additionally includes a pipette tip receiving means 35 which is realized such that the pipette tip 21 is able to be inserted into the receiving portion up to a stop or a positive locking or non-positive locking receiving means. Consequently, the pipette tip 21 can be deposited in the receiving device without it falling into a bag. The receiving device 18 comprises a dosing head 22 which is realized so as to be displaceable along the receiving device 18. In addition, the dosing head 22 can be connected to the pipette tip 21. The dosing head 22 comprises a pipette tip connector 25 for this purpose as well as a feeding connector 26 for feeding the dilution liquid. A release mechanism 27 is actuated in order to release a pipette tip 21 from the dosing head 22. The release mechanism 27 is part of the dosing head 22. The release mechanism 27 is rotationally mounted on one side and can be removed from the dosing head 22 by actuating a pipette tip 21. A pipette tip 21 with a higher grade dilution as well as a second pipette tip 21 with the lower dilution is used for each receiving portion 20. A dosing head repository 41 is realized to store the dosing head when not in use. At the same time, the dosing head repository protects the pipette tip connector 25 from contamination. The dosing head 22 additionally includes a push button 42 which can be connected electronically to a dispenser (see FIG. 3). The push button 42 triggers the inflow of dilution liquid.

Figure 10:
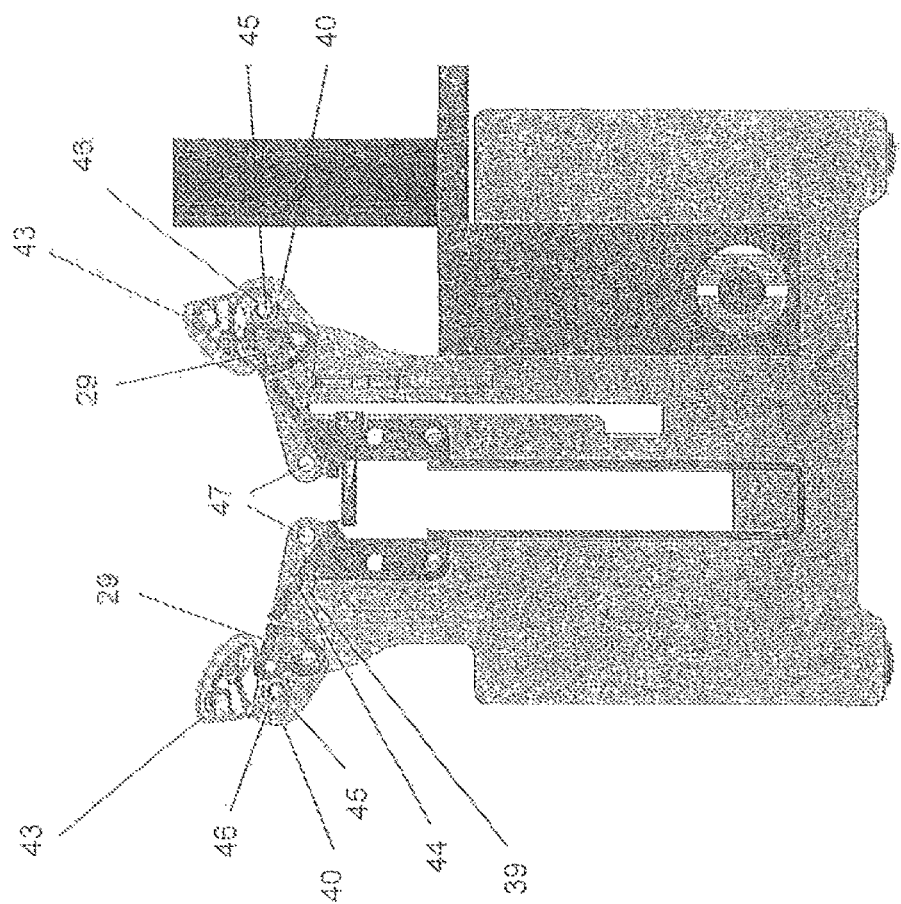
FIG. 10 shows a cross section through a flap mechanism.

FIG. 10 shows a cross section through a flap mechanism 39. The side parts 43 of the flaps 40 are arranged so as to be pivotable about a pivot axis 45 and are held in their position by springs 46. The side part 43 rests in the starting position (FIG. 8a) on the contact surface 29. The flaps 40 are once again arranged so as to be pivotable about the flap axis 47. The flaps 40 are also shown in a neutral position. In order to release the tongues of a bag from the contact surface 29 (see FIG. 8g), the flaps 40 can be pressed down in the direction away from the side parts 43 against a further spring (not shown) such that the bag is suspended from the pipette table 44. In addition, the flaps 40 can be pressed toward one another such that the side parts 43 are hinged up against the spring force of the spring 46. In this connection, the pivot axis 45 is arranged in an eccentric manner with respect to the pivot point of the said parts 43 such that the side parts hinge up as soon as a pressure is applied on the side parts.

The invention claimed is:

1. A bag for carrying out dilution series, said bag including:
   at least one receiving region for adding at least one of a sample and a dilution liquid and for removing diluted medium, and
   at least one mixing region for collecting and mixing the sample and the dilution liquid,
   wherein the at least one mixing region is sealed in a liquid-tight manner only along three sides and the at least one receiving region delimits the mixing region via a spot weld along a fourth side, and the at least one receiving region comprises at least two tongues, wherein said tongues extend along an entire length of the receiving region and can be folded over in opposite directions, away from one another, up to the mixing region,
   wherein a wall of thickness of the bag is less than or equal to 30 μm.

2. The bag as claimed in claim 1, wherein the bag is developed so as to be non-self-supporting.

3. The bag as claimed in claim 1, wherein the bag includes two foils.

4. The bag as claimed in claim 1, wherein the bag is connected along the three sides.

5. The bag as claimed in claim 1, wherein the receiving region includes two pipette tip ports which are realized separately from one another as a result of a connection.

6. The bag as claimed in claim 1, wherein a connection on the sides of the mixing region does not include sides of the receiving region.

7. The bag as claimed in claim 1, wherein a first receiving region is realized so as to be severable from a second or adjacent receiving region.

8. The bag as claimed in claim 1, wherein the receiving region is developed such that no dead corners are realized and a vortex generation is achievable for optimum intermixing.

9. The bag as claimed in claim 1, wherein a welding connection on the sides of the mixing region does not include sides of the receiving region.

10. The bag as claimed in claim 1, wherein the tongues of the bag are foldable in opposite directions away from one another.

* * * * *